(12) United States Patent
Aboytes et al.

(10) Patent No.: US 9,375,333 B1
(45) Date of Patent: Jun. 28, 2016

(54) IMPLANTABLE DEVICE DETACHMENT SYSTEMS AND ASSOCIATED DEVICES AND METHODS

(71) Applicant: Medina Medical, Inc., Menlo Park, CA (US)

(72) Inventors: Maria Aboytes, Palo Alto, CA (US); Ricardo Aboytes, Palo Alto, CA (US); Abraham Van Scoit, Los Gatos, CA (US); Gil LaRoya, Santa Clara, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/641,175

(22) Filed: Mar. 6, 2015

(51) Int. Cl.
*A61F 2/95* (2013.01)

(52) U.S. Cl.
CPC ........... *A61F 2/95* (2013.01); *A61F 2002/9522* (2013.01)

(58) Field of Classification Search
CPC .................. A61B 17/12113; A61B 17/12118; A61B 17/12122; A61B 17/12145; A61B 17/1215; A61B 2017/1205; A61B 2017/12054; A61B 2017/12095; A61B 17/12022; A61F 2002/9511; A61F 2/966; A61F 2002/9522; A61F 2002/9505; A61F 2/95
USPC ............................................... 623/1.11, 1.23
See application file for complete search history.

(56) References Cited

U.S. PATENT DOCUMENTS

| | | |
|---|---|---|
| 5,250,071 A | 10/1993 | Palermo |
| 5,645,558 A | 7/1997 | Horton |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,814,062 A | 9/1998 | Sepetka et al. |
| 5,911,731 A | 6/1999 | Pham et al. |
| 5,916,235 A | 6/1999 | Guglielmi |

(Continued)

FOREIGN PATENT DOCUMENTS

| | | |
|---|---|---|
| EP | 2208483 A1 | 7/2010 |
| JP | 2005261951 | 9/2005 |

(Continued)

OTHER PUBLICATIONS

International Search Report for International Application No. PCT/US2013/077767, mailed on Mar. 19, 2014, 14 pages.

(Continued)

*Primary Examiner* — Jonathan W Miles
*Assistant Examiner* — George J Ulsh

(57) ABSTRACT

Systems, devices, and methods for detaching an implantable device from a delivery system are disclosed herein. One aspect of the present technology, for example, is directed toward a system that includes an elongated shaft having a first coupling element with a first opening, an implantable device having a second coupling element with a second opening, and an elongated member configured to extend through the shaft. The system can have a retained state in which the elongated member is positioned through the first opening and the second opening, and a released state in which the elongated member is removed from the second opening and the first coupling element is configured to move proximally apart from the second coupling element with an axial displacement not greater than an outer diameter of the first coupling element at a location along the length of the first coupling element proximate the first opening.

36 Claims, 11 Drawing Sheets

(56) References Cited

U.S. PATENT DOCUMENTS

| | | |
|---|---|---|
| 5,925,060 A | 7/1999 | Forber |
| 5,928,260 A | 7/1999 | Chin et al. |
| 5,935,148 A | 8/1999 | Villar et al. |
| 5,944,738 A | 8/1999 | Amplatz et al. |
| 5,951,599 A | 9/1999 | McCrory |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,168,615 B1 | 1/2001 | Ken et al. |
| 6,168,622 B1 | 1/2001 | Mazzocchi |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford, III et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,556 B1 | 11/2003 | VanTassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,486 B2 | 2/2004 | Ho et al. |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,905,503 B2 | 6/2005 | Gifford, III et al. |
| 6,936,055 B1 | 8/2005 | Ken et al. |
| 6,991,617 B2 | 1/2006 | Hektner et al. |
| 6,994,092 B2 | 2/2006 | van der Burg et al. |
| 6,994,717 B2 | 2/2006 | Konya et al. |
| 7,011,671 B2 | 3/2006 | Welch |
| 7,029,487 B2 | 4/2006 | Greene, Jr. et al. |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,326,225 B2 | 2/2008 | Ferrera et al. |
| 7,331,980 B2 | 2/2008 | Dubrul et al. |
| 7,419,503 B2 | 9/2008 | Pulnev et al. |
| 7,597,704 B2 | 10/2009 | Frazier et al. |
| 7,708,754 B2 | 5/2010 | Balgobin et al. |
| 8,142,456 B2 | 3/2012 | Rosqueta et al. |
| 8,211,160 B2 | 7/2012 | Garrison et al. |
| 8,333,783 B2 | 12/2012 | Braun et al. |
| 8,343,167 B2 | 1/2013 | Henson |
| 8,834,515 B2 | 9/2014 | Win et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0028209 A1 | 2/2003 | Teoh et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2005/0222580 A1 | 10/2005 | Gifford et al. |
| 2005/0277978 A1 | 12/2005 | Greenhalgh |
| 2006/0034883 A1 | 2/2006 | Dang et al. |
| 2006/0052816 A1 | 3/2006 | Bates et al. |
| 2006/0064151 A1 | 3/2006 | Guterman et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1* | 6/2006 | Sepetka et al. ............... 606/200 |
| 2006/0155323 A1 | 7/2006 | Porter et al. |
| 2006/0190070 A1 | 8/2006 | Dieck et al. |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0219619 A1 | 9/2007 | Dieck et al. |
| 2007/0276426 A1 | 11/2007 | Euteneuer |
| 2007/0276427 A1 | 11/2007 | Euteneuer |
| 2007/0288083 A1 | 12/2007 | Hines |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0200945 A1 | 8/2008 | Amplatz et al. |
| 2008/0200979 A1 | 8/2008 | Dieck et al. |
| 2008/0221600 A1 | 9/2008 | Dieck et al. |
| 2008/0281350 A1 | 11/2008 | Sepetka et al. |
| 2009/0043375 A1 | 2/2009 | Rudakov et al. |
| 2009/0062899 A1 | 3/2009 | Dang et al. |
| 2009/0112251 A1 | 4/2009 | Qian et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0297582 A1 | 12/2009 | Meyer et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0139465 A1 | 6/2010 | Christian et al. |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |

(56) References Cited

U.S. PATENT DOCUMENTS

| | | |
|---|---|---|
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | deBeer |
| 2011/0137332 A1 | 6/2011 | Sepetka et al. |
| 2011/0144669 A1 | 6/2011 | Becking et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283769 A1 | 11/2012 | Cruise et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0116722 A1 | 5/2013 | Aboytes et al. |

FOREIGN PATENT DOCUMENTS

| | | |
|---|---|---|
| JP | 2008521492 | 6/2008 |
| WO | 2006034149 | 3/2006 |
| WO | 2008074027 | 6/2008 |
| WO | WO-2009/014528 A1 | 1/2009 |
| WO | 2010027363 | 3/2010 |
| WO | WO-2010/077599 A1 | 7/2010 |
| WO | WO-2012/034135 A1 | 3/2012 |
| WO | WO-2013/138615 A2 | 9/2013 |

OTHER PUBLICATIONS

International Search Report and Written Opinion for International Application No. PCT/US2013/031466, mailed on Jun. 25, 2014, 8 pages.

International Search Report and Written Opinion for International Application No. PCT/US11/51268, mailed on Jan. 2, 2012, 7 pages.

Office Action issued in U.S. Appl. No. 13/421,122, mailed Dec. 26, 2013, 12 pages.

Office Action issued in U.S. Appl. No. 13/230,628, mailed on Jul. 18, 2013, 17 pages.

Office Action issued in U.S. Appl. No. 13/230,628, mailed on Jun. 4, 2014, 16 pages.

\* cited by examiner

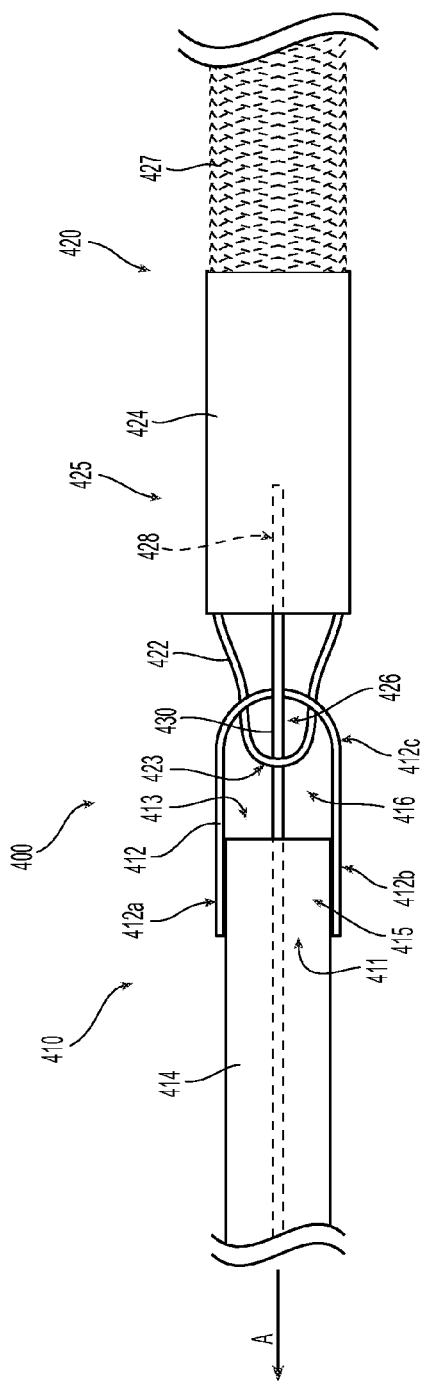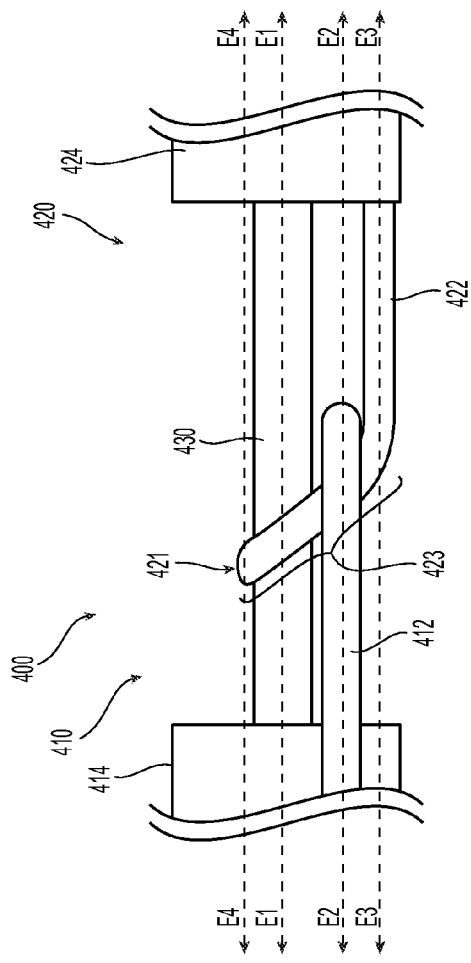
*Fig. 4A*
*Fig. 4B*

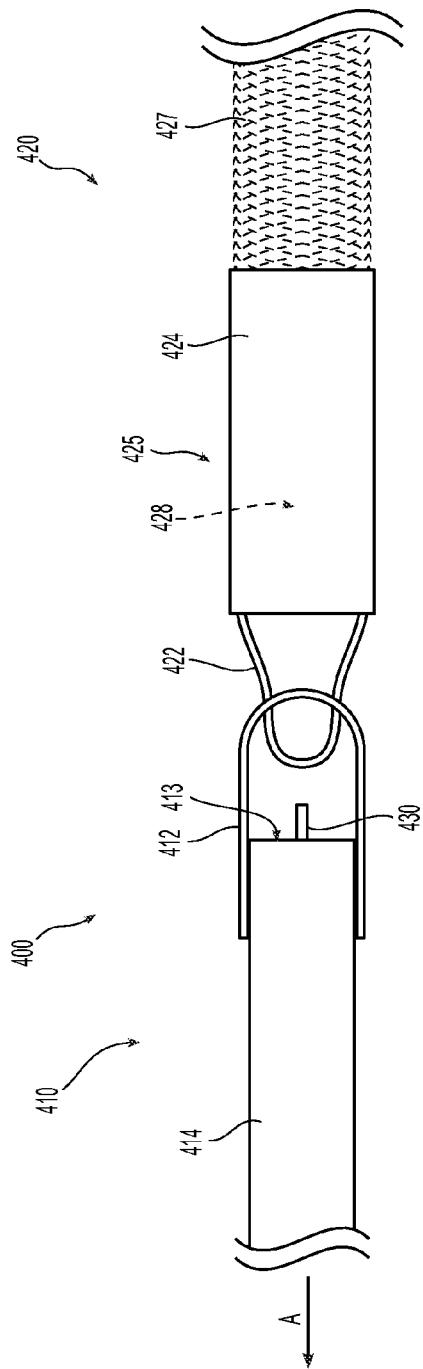
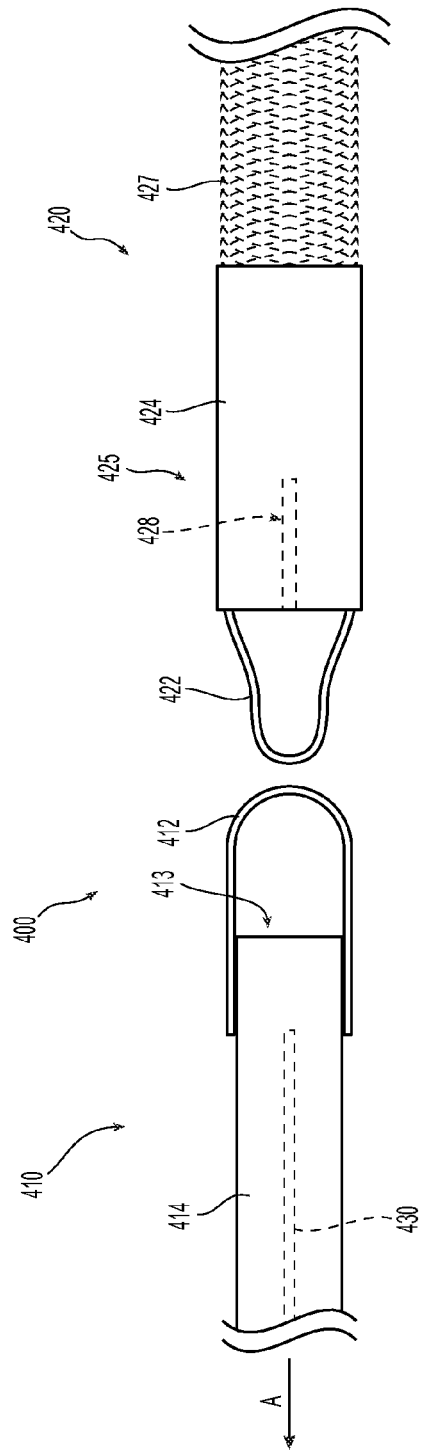

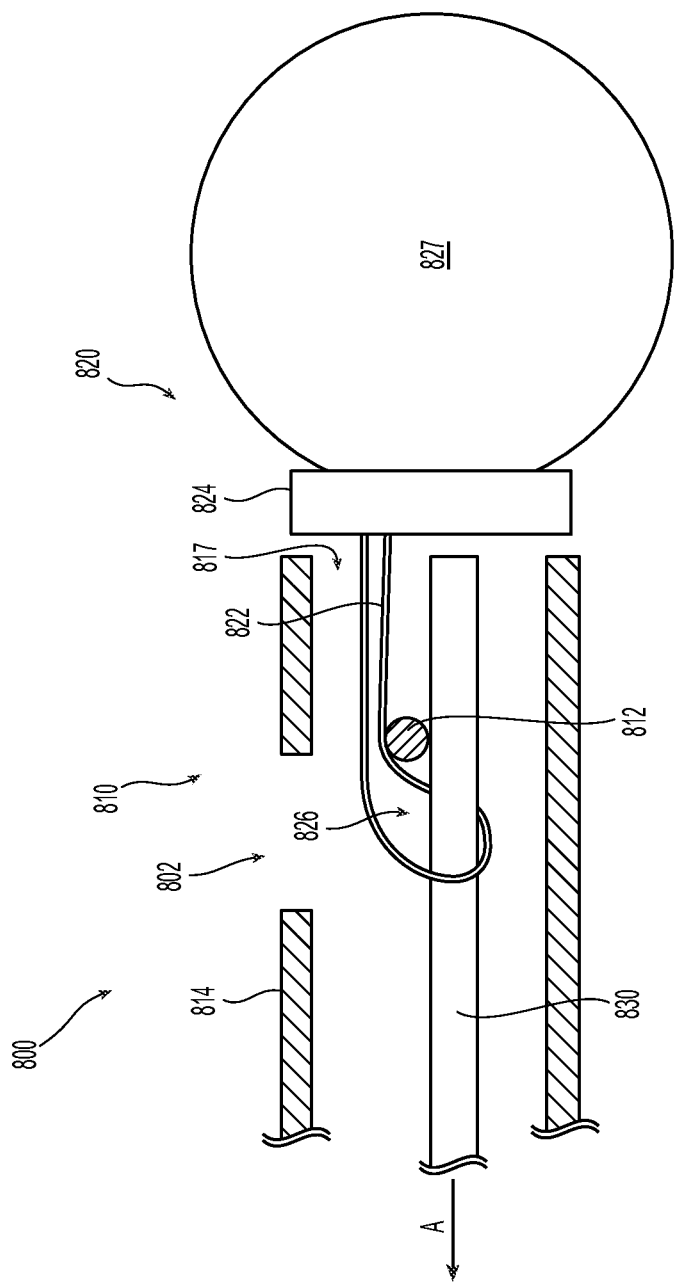

IMPLANTABLE DEVICE DETACHMENT SYSTEMS AND ASSOCIATED DEVICES AND METHODS

TECHNICAL FIELD

The present technology relates generally to devices, systems, and methods for delivering implantable devices to a target site or location within the body of a patient. Many embodiments of the present technology relate to devices, systems, and methods for securing an implantable device to a delivery system and detaching an implantable device from a delivery system.

BACKGROUND

The use of catheter delivery systems for positioning and deploying therapeutic devices in the vasculature of the human body has become a standard procedure for treating endovascular diseases. Such devices are particularly useful in treating areas where traditional operational procedures are impossible or pose a great risk to the patient, for example in the treatment of aneurysms in intracranial blood vessels. Due to the delicate tissue surrounding intracranial blood vessels, such as brain tissue, it is very difficult and often risky to perform surgical procedures to treat defects of the intracranial blood vessels. Advancements in catheter deployment systems have provided an alternative treatment in such cases. Typically, these procedures involve inserting a delivery catheter containing a vascular occlusion device into the vasculature of a patient and guiding it through the vasculature to a predetermined delivery site. The delivery catheter also contains a delivery member attached to the vascular occlusion device which can be used to push the occlusion device out of the distal end of the delivery catheter into the delivery site. Some of the problems associated with these procedures relate to ensuring that the occlusion device does not prematurely detach from the delivery member and/or delivery catheter, as well as ensuring the complete release and deployment of the occlusion device. Accordingly, there is a need for devices and methods that address one or more of these deficiencies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

In FIGS. 3A and 3B, the handle assembly is shown in a retained state.

FIG. 4A is top view of a detachment system in a retained state configured in accordance with another embodiment of the present technology.

FIG. 4B is an enlarged side view of a portion of the detachment system of FIG. 4A in a retained state.

FIGS. 5A and 5B are top views of the detachment system of FIGS. 4A and 4B during withdrawal of the elongated member and shaft configured in accordance with the present technology.

FIG. 8 is partial cross-sectional side view of a detachment system in a retained state configured in accordance with another embodiment of the present technology.

DETAILED DESCRIPTION

The present technology provides devices, systems, and methods for securing an implantable device to a delivery system and controllably detaching the implantable device from the delivery system. The devices, systems, and methods of the present technology provide several advantages over conventional detachment systems. For example, the devices, systems, and methods of the present technology firmly secure an implantable device to a delivery system without incorporating a spherically- or ball-shaped coupling element. Because of this, the detachment devices and systems of the present technology are easier to manufacture than conventional detachment systems that incorporate such ball-shaped coupling elements that require tight tolerances due to their small size. Another advantage of the present technology is that the elongated member is positioned within a portion of the implantable device, thereby preventing axial displacement of the system in the retained state. Several conventional devices include an articulating joint between the delivery system and the implantable device (e.g., including systems incorporating a ball-shape coupling element) that allow the implantable device to move out of axial alignment with the delivery system during delivery and release of the implantable device. Other conventional devices have a fixed joint between the delivery system and the implantable device and require the implantable device to move out of axial alignment with the delivery system during delivery and release of the implantable device. The detachment systems of the present technology are configured to axially align the implantable device and the delivery system and maintain the axial alignment throughout delivery and release of the implantable device. Additionally, because of this maintained axial alignment, stress caused by the manipulation of the delivery system during insertion into the blood vessel can be absorbed by both the delivery system and the implantable device, thereby reducing fatigue at their mechanical junction.

Specific details of several embodiments of detachment devices, systems, and methods in accordance with the present technology are described below with reference to FIGS. 1A-8. With regard to the terms "distal" and "proximal" within this description, unless otherwise specified, the terms can reference a relative position of the portions of an implantable device and/or an associated catheter device with reference to an operator and/or a location in the vasculature.

Figure 1A:
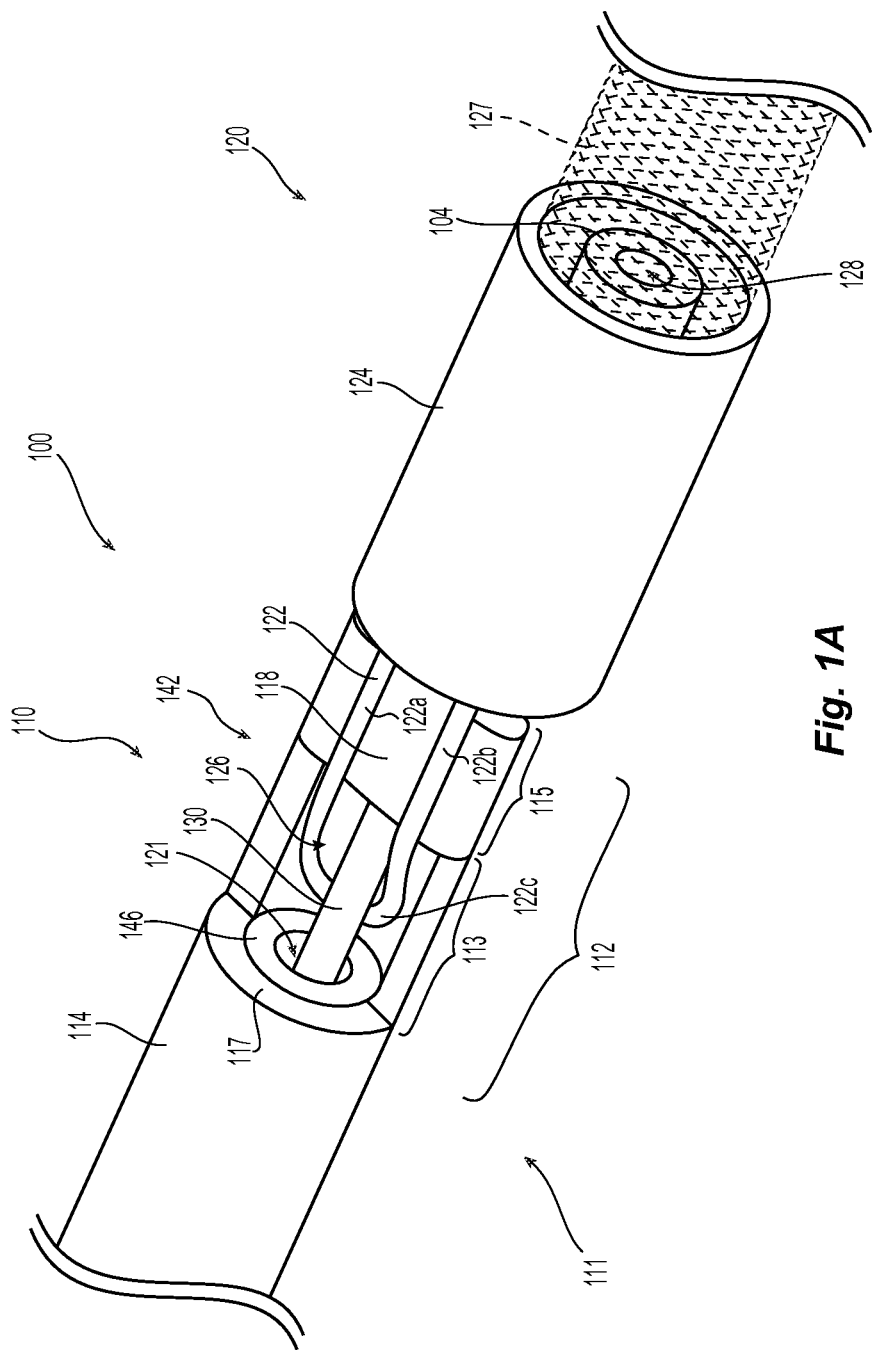
FIG. 1A is a perspective view of a detachment system in a retained state configured in accordance with an embodiment of the present technology.
Figure 1B:
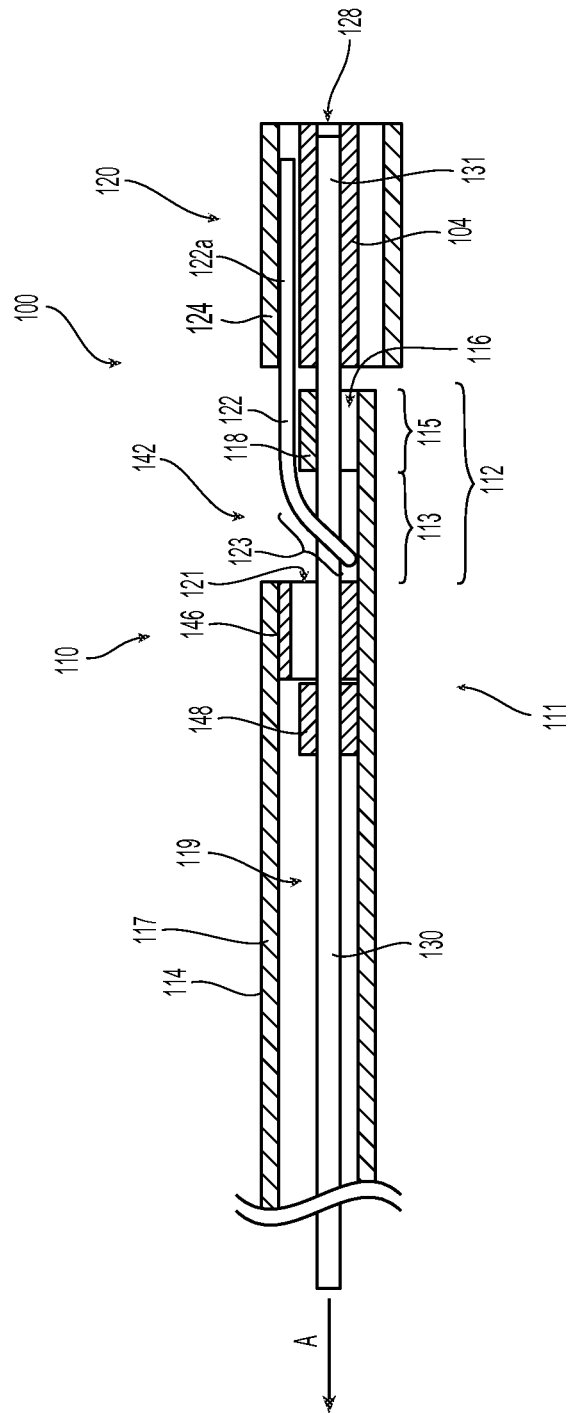
FIG. 1B is a partial cross-sectional side view of the detachment system of FIG. 1A in a retained state configured in accordance with an embodiment of the present technology. The expandable component of FIG. 1A is not shown in FIG. 1B for purposes of illustration.

I. Selected Embodiments of Detachment Systems and Associated Devices and Methods FIGS. 1A and 1B are a top perspective view and a partial cross-sectional side view, respectively, of one embodiment of a detachment system 100 (also referred to as the "system 100") in a retained state configured in accordance with the present technology. Referring to FIGS. 1A-1B together, the system 100 can include a catheter 110, an implantable device 120, and an elongated member 130. For purposes of illustration, only a portion of the catheter 110, the implantable device 120, and the elongated member 130 are shown in FIGS. 1A-1B. The catheter 110 can include an elongated shaft 114 having a proximal portion (not shown) and a distal portion 111 configured to be intravascularly positioned at a treatment site within a blood vessel (e.g., a small blood vessel) of a human patient. The distal portion 111 can include a first coupling element 112 configured to slidably receive a portion of the elongated member 130 therethrough. The implantable device 120 can include an expandable component 127 (a portion is shown in FIG. 1A only) configured to at least partially fill an aneurysm (e.g., a cerebral aneurysm) at the treatment site. The implantable device 120 can include a second coupling element 122 configured to slidably receive the elongated member 130. As described in greater detail below, the system 100 can be transformable between a retained state in which the elongated member 130 extends through both the first and second coupling elements 112, 122 to secure the implantable device 120 to the catheter 110, and a released state in which the elongated member 130 has been withdrawn proximally of the second coupling element 122 to thereby release the implantable device 120 from the shaft 114.

The elongated shaft 114 in the embodiment shown in FIGS. 1A and 1B includes a tubular sidewall 117 (e.g., a hypotube) that defines a lumen 119 (FIG. 1B) configured to slidably receive the elongated member 130. The lumen 119 can extend distally from the proximal portion (not shown) of the shaft 114 to an opening 121 at the distal portion of the shaft 114. In some embodiments, the shaft 114 can be configured to be slidably received by a guide catheter and/or delivery catheter (e.g., a microcatheter), as is known in the art. In some embodiments, the shaft 114 includes a detent 146 positioned at least partially within the lumen 119 proximal of the first coupling element 112, and the system 100 further includes a protrusion 148 (FIG. 1B) coupled to or associated with an outer surface of the elongated member 130. During advancement of the shaft 114 to a treatment site through a tortuous vascular pathway (such as within a cranial blood vessel), the tortuosity and curvature of the vasculature can exert frictional forces against the delivery system. As such, a certain amount of slack is often built into the length of the shaft 114. When the delivery catheter (not shown) overcomes the frictional forces, the delivery catheter and/or shaft 114 can unexpectedly jump forward. When this occurs, the protrusion 148 and/or detent 146 operate together to prevent the elongated member 130 from jumping forward too far and pushing the implantable device 120 out of the delivery catheter (not shown) prematurely. In other embodiments, the shaft 114 may not include a detent 146 and/or a protrusion 148.

In the embodiments shown in FIGS. 1A-1B, the first coupling element 112 is integral with or formed by a portion of the sidewall 117. In other embodiments, the first coupling element 112 can be a component separate from the sidewall 117 and coupled to the shaft 114 during manufacturing. The first coupling element 112 can include a first region 113 and a second region 115 that are configured to slidably receive the elongated member 130 therethrough. The first region 113 can include an opening 142 configured to receive a portion of the second coupling element 122. For example, when the sidewall 117 defines a portion of the first coupling element 112, a portion of the sidewall 117 can be removed during manufacturing (e.g., via laser cutting or other suitable techniques) such that a remaining portion of the sidewall 117 along the first region 113 can have a c-shaped or semi-circular cross-section. In other embodiments, the sidewall 117 along the first region 113 can have other suitable shapes and/or configurations depending on the shape and size and of the opening 142. It will be appreciated that a length of the first region 113 can be selected to improve the pushability of the system 100 during delivery of the implantable device 120.

The second region 115 of the first coupling element 112 can include a cover 118 extending between opposing portions of the sidewall 117. The cover 118 and the sidewall 117 can together enclose a passageway or lumen 116 (FIG. 1B) configured to slidably receive the elongated member 130 therethrough. The lumen 116 can extend distally from an opening adjacent the first region 113 to an opening positioned at a distal terminus of the shaft 114 and/or the first coupling element 112. In some embodiments the cover 118 can be a separate piece attached to the sidewall 117 during manufacturing, and in other embodiments the cover 118 can be integral with the sidewall 117. It will be appreciated that the second region 115 can have any desired length based on the length of the cover 118. As such, in selected embodiments where the system 100 has a relatively short cover 118, the second region 115 can include a single opening rather than two openings flanking a lumen.

The implantable device 120 can include the expandable component 127 (shown in a collapsed or low-profile state in FIG. 1A), a cylindrical hub 124 coupled to a proximal portion of the expandable component 127, and the second coupling element 122. In some embodiments the expandable component 127 can be a vascular occlusion device. The expandable component 127 can be a braid, and one end of the braid can be attached to the hub 124. Examples of expandable braids suitable for use with the detachment systems of the present technology are described in U.S. patent application Ser. No. 13/230,628, filed Sep. 12, 2011, and U.S. patent application Ser. No. 13/727,029, filed Dec. 26, 2012, both of which are incorporated herein by reference in their entireties. The hub 124 can have any suitable size, shape and/or configuration, and/or all or a portion of the hub 124 can be coated with or made of a radiopaque material to improve visualization of the implantable device 120 during and/or after implantation. The second coupling element 122 can be coupled to an inner surface of the hub 124 via adhesive, soldering, welding, and/or other suitable mechanical fixation means). In other embodiments, the second coupling element 122 can be integral with the hub 124, coupled to an outer surface of the hub 124, and/or coupled directly to the expandable component 127. In still other embodiments, the implantable device 120 may not include a hub 124 and the second coupling element 122 can be coupled directly to the expandable component 127.

In some embodiments, the implantable device 120 can include a collar 104 coaxially positioned within the hub 124.

The collar 104 can have a lumen 128 configured to slidably receive a distal portion 131 (FIG. 1B) of the elongated member 130. A proximal portion of expandable component 127 can be positioned around the outer periphery of the collar 104. An inner diameter of the lumen 128 can be greater than that of the elongated member 130 such that a small gap exists between the lumen 128 and the elongated member 130 to reduce the friction between the elongated member 130 and the collar 104 and improve the ease of withdrawal of the elongated member 130 from the lumen 128 and/or implantable device 120. Although the collar 104 is shown having a cylindrical shape in FIG. 1A, in other embodiments the collar 104 can have any suitable size, shape and/or configuration. Additionally, all or a portion of the collar 104 can be coated with or made of a radiopaque material to improve visualization of the implantable device 120 during and/or after implantation. In particular embodiments, the system 100 may not include a collar 104. For example, in some embodiments the proximal portion of the expandable component 127 can be distributed around and fixed to an interior surface of the hub 124 such that a cavity remains within the hub 124 surrounded by the proximal portion of the expandable component 127.

The second coupling element 122 can have an opening 126 (FIG. 1A) configured to slidably receive the elongated member 130 therethrough. At least a portion of the second coupling element 122 can be configured to extend proximally beyond the second region 115 of the first coupling element 112 and into the opening 142. In the embodiment shown in FIG. 1A, the second coupling element 122 is u-shaped. For example, in the embodiment shown in FIGS. 1A-1B, the second coupling element 122 includes first and second legs 122a, 122b (second leg 122b not shown in FIG. 1B) and an intermediate portion 122c between the legs 122a-b. As such, the first and second legs 122a, 122b, the intermediate portion 122c and a proximal portion of the hub 124 and/or expandable component 127 together define a closed path surrounding the opening 126. The legs 122a, 122b can be generally linear and can each include a first portion positioned along and fixed to an interior surface of the hub 124 and a second portion extending proximally from the hub 124. In other embodiments, all or portions of each of the legs 122a, 122b can have other suitable shapes and configurations (e.g., non-linear configurations). Moreover, in the illustrated embodiment, at least a portion of the intermediate portion 122c is curved. In other embodiments, all or portions of the intermediate portion 122c can have other suitable shapes and configurations (e.g., a square shape, a triangular shape, etc.).

In some embodiments, all or a portion of the second coupling element 122 can be flexible. For example, the second coupling element 122 can be configured to bend at least in a direction that is transverse to a longitudinal axis of the first coupling element 112 (as described in greater detail below with respect to FIGS. 2A-2D). As shown in FIG. 1B, the second coupling element 122 can be configured to bend towards the elongated member 130. In other embodiments, the second coupling element 122 can be configured to bend in any direction. In some embodiments, the second coupling element 122 can be made of a thin metal wire (e.g., nitinol or stainless steel) having a diameter that is less than about 0.004 inches. In a particular embodiment, the wire can have a diameter that is less than about 0.003 inches (e.g., about 0.002 inches, about 0.001 inches, etc.) In other embodiments (not shown), all or a portion of the second coupling element 122 can be rigid (e.g., stainless steel, a plastic, and/or any material with a suitable thickness to avoid bending or flexing during use) and/or highly flexible (e.g., a thread or filament).

Referring still to FIGS. 1A-1B, when the system 100 is in the retained state, a portion of the second coupling element 122 is positioned proximally of the second region 115 of the first coupling element 112 and in the opening 142 of the first coupling element 112 such that the opening 126 in the second coupling element 122 is at least partially aligned with the lumen 116 of the first coupling element 112. For example, at least when the system 100 is in the retained state, the second coupling element 122 can include an inclined portion 123 (FIG. 1B) that forms an acute or obtuse angle (e.g., not a 90 degree angle) with respect to a central longitudinal axis of the second coupling element 122. As such, when the system 100 is in the retained state, the elongated member 130 can extend distally from the proximal portion of the catheter 110 through the shaft lumen 119, through the opening 126 in the second coupling element 122, through the lumen 116 of the first coupling element 112, and into a proximal portion of the implantable device 120. While the elongated member 130 is positioned through the opening 126 and at least partially within the lumen 116, the implantable device 120 is tethered to or otherwise retained with the shaft 114. In this retained configuration, a central longitudinal axis of the elongated shaft 114 can be generally aligned with a central longitudinal axis of the implantable device 120 so as to reduce the overall profile of the system 100.

Figure 2A:
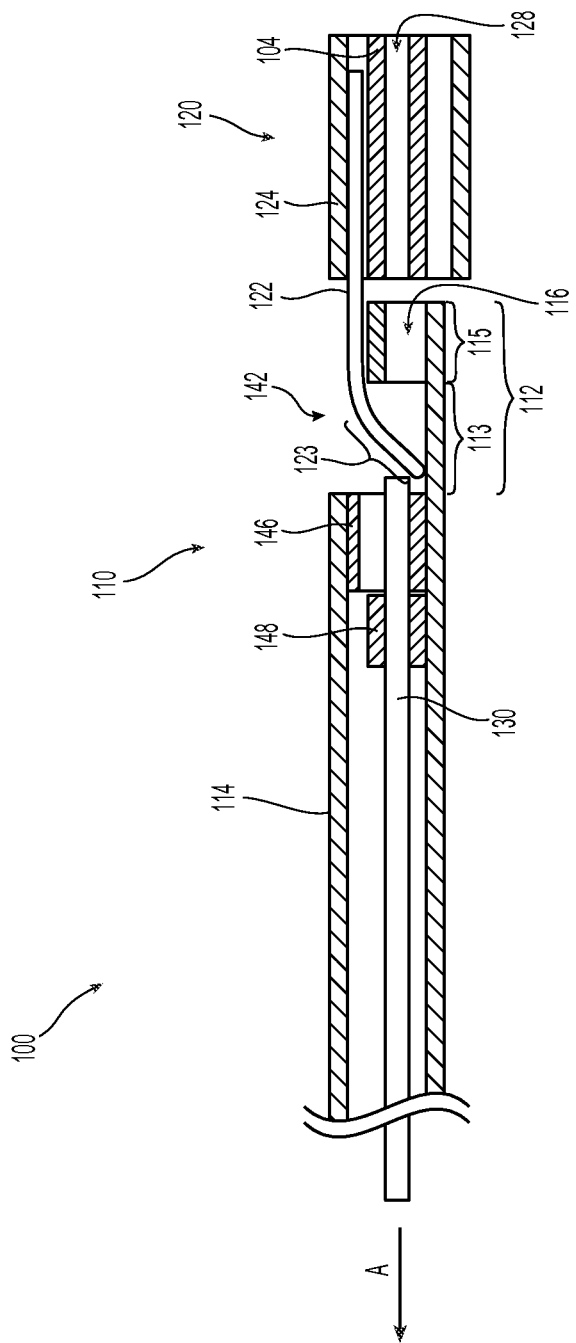
FIG. 2A is a partial cross-sectional side view of the detachment system shown in FIG. 1A in a released state configured in accordance with an embodiment of the present technology.

FIG. 2A is a partial cross-sectional side view of the system 100 in the released state configured in accordance with an embodiment of the present technology. As shown in FIG. 2A, when the elongated member 130 is withdrawn proximally (as indicated by arrow A) through the lumen 116 and the opening 126 to a position proximal of the second coupling element 122, the implantable device 120 is decoupled from the shaft 114. Upon proper positioning and release of the implantable device 120, the shaft 114 can be withdrawn from the treatment site.

The detachment systems of the present technology are particularly useful in small vessels or other body lumens with limited space. In intracranial vessels, for example, it can be advantageous to reduce and/or eliminate axial displacement of the shaft 114 and/or the implantable device 120 from their respective central longitudinal axes as the shaft 114 is removed from the patient immediately after removing the elongated member 130 from the opening 126 (FIG. 1A) and lumen 116. For example, FIG. 2A shows the detachment system 100 immediately after the elongated member 130 has been removed from the opening 126 (FIG. 1A) and lumen 116. Several aspects of one or more embodiments of the present technology can reduce and/or eliminate such axial displacement of the system 100, particularly in embodiments of the present technology where a portion of the second coupling element 122 is configured to remain between a portion of the first coupling element 112 and a catheter 110 withdrawal path A even after the elongated member 130 has been withdrawn. For example, as shown in FIG. 2B, the inclined portion 123 of the second coupling element 122 can remain positioned proximal to the second region 115 of the first coupling element 112 and at an elevation that positions the inclined portion 123 between the second region 115 and a catheter device withdrawal path A.

As a preliminary matter, the term "axial displacement" as used herein refers to an axial displacement of the implantable device 120 and/or the shaft 114 from their respective axial positions in the retained state. "Substantial axial displacement" as used herein refers to a displacement that is greater than or equal to an outer diameter (or width, if not a circular shape) of the smaller of the second region 115 and the second coupling element 122. For example, the outer diameter can be that of the first coupling element 112 at a location along the length of the first coupling element 112 longitudinally aligned with a proximal portion of the lumen 116 (FIG. 2A). Additionally, the term "without substantial axial displacement" as used herein can include no or close to no axial displacement (e.g., an axial displacement of 0.000 inches, an axial displacement of 0.001 inches.

Figure 2B:
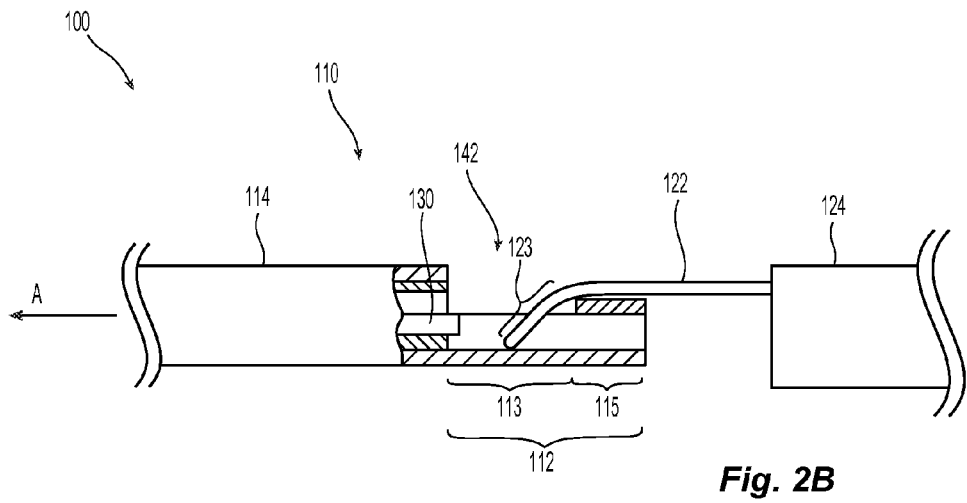
FIGS. 2B-2C are partial cross-sectional side views.
Figure 2C:
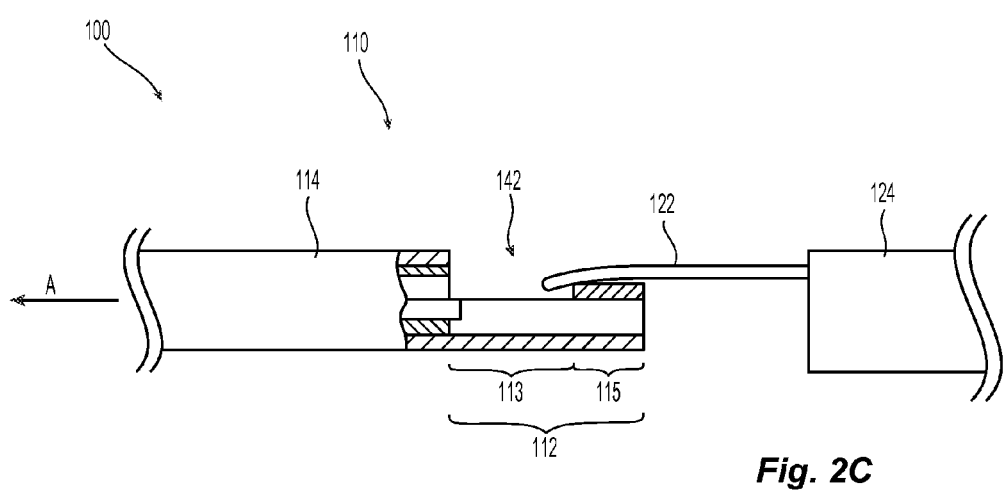
Figure 2D:
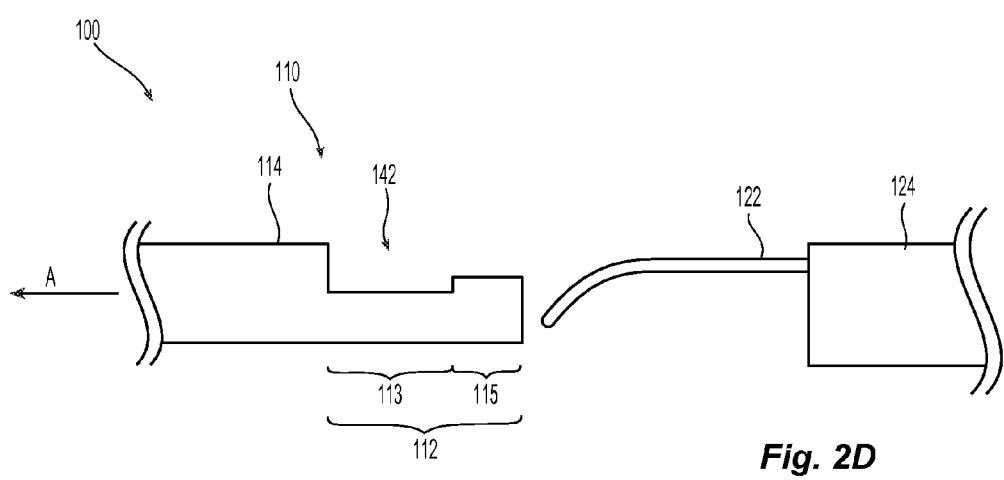
FIG. 2D is a side view, that together show the detachment system of FIGS. 1A-2A during withdrawal of the delivery system configured in accordance with an embodiment of the present technology.

As shown in FIGS. 2B-2D, in those embodiments where the second coupling element 122 is flexible, the second coupling element 122 can bend or flex out of the withdrawal path A of the second region 115 without substantial axial displacement of the implantable device 120 and without extending beyond the profile of the system 100. For example, as shown in FIG. 2C, as the shaft 114 is moved proximally along the withdrawal path A, the inclined portion 123 flexes or bends as the second region 115 of the first coupling element 112 slides under the second coupling element 122 without substantially axially displacing the implantable device 120 and/or the shaft 114. In other words, in the released state and as the elongated shaft 114 moves proximally, the system 100 is configured such that the first coupling element 112 slides proximally along the second coupling element 122 within a circumference of the elongated shaft 114.

In other embodiments (not shown), at least a portion of the second coupling element 122 can be made of a shape-memory material that, upon release from the elongated member 130, assumes a shape or position that is outside of the withdrawal path A. As such, the first coupling element 112 may be pulled proximally past the second coupling element 122 without engaging the second coupling element 122.

In yet other embodiments (not shown), at least when the system 100 is in the retained state, the first coupling element 112 and/or the second coupling element 122 can have a ramped or inclined surface that can reduce axial displacement of the shaft 114 and/or the implantable device 120 during withdrawal of the shaft 114. The inclined surface of the first and/or second coupling element 112, 122 can be configured to oppose and/or engage an inclined or non-inclined portion of the other of the first or second coupling element 112, 122. For example, the first and/or second coupling element 112, 122 can be rigid and maintain an inclined state in both the retained and released states. In other embodiments, the first and/or second coupling element 112, 122 can be flexible material and assume an inclined state in one or both of the retained and released states.

Figure 3A:
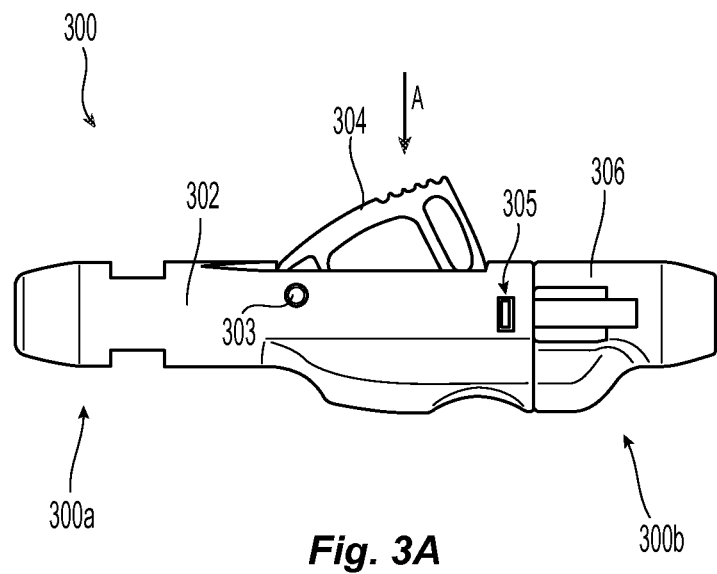
FIG. 3A is an isolated side view of a handle assembly configured in accordance with the present technology.
Figure 3B:
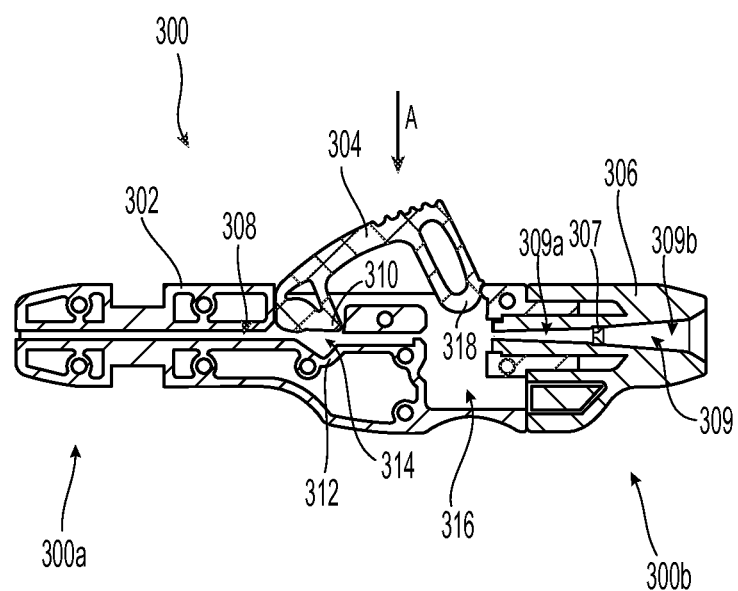
FIG. 3B is a cross-sectional side view of the handle assembly of FIG. 3A shown coupled to an elongated member configured in accordance with the present technology.

II. Selected Embodiments of Delivery Systems and Methods for use with the Detachment Systems of the Present Technology FIGS. 3A and 3B are isolated side and isolated cross-sectional side views, respectively, of one embodiment of a handle assembly 300, shown in a retained state, configured for use with the detachment systems of the present technology. Referring to FIGS. 3A-3B, the handle assembly 300 can have a proximal portion 300a and a distal portion 300b. The handle assembly 300 can include a housing 302, a lever 304 coupled to the housing 302, and a collar 306 positioned at the distal portion 300b. The lever 304 can be coupled to the housing 302 and is moveable between a retained state (FIGS. 3A-3C) in which an implantable device is retained by the detachment system, and a released state (FIG. 3E) in which the implantable device has been released from the detachment system. In some embodiments, the lever 304 can be configured to pivot and/or rotate relative to the housing (e.g., about axis 303). In other embodiments (not shown), the lever 304 can be a flexible cantilever having a portion fixed to the housing 302 and a free end configured to move towards the housing 302 as the lever 304 is bent or flexed towards the housing 302 (indicated by arrow A). In some embodiments, the lever 304 can include one or more protrusions configured to be received by one or more cavities in the housing 302. For example, as shown in FIG. 3B, the lever 304 can include a first protrusion 310 and a second protrusion 318 positioned distal to the first protrusion 310 along the length of the lever 304. In other embodiments, the lever 304 can include more or fewer than two protrusions (e.g., one protrusion, three protrusions, etc.) and/or can have other suitable shapes and/or configurations.

Figure 3C:
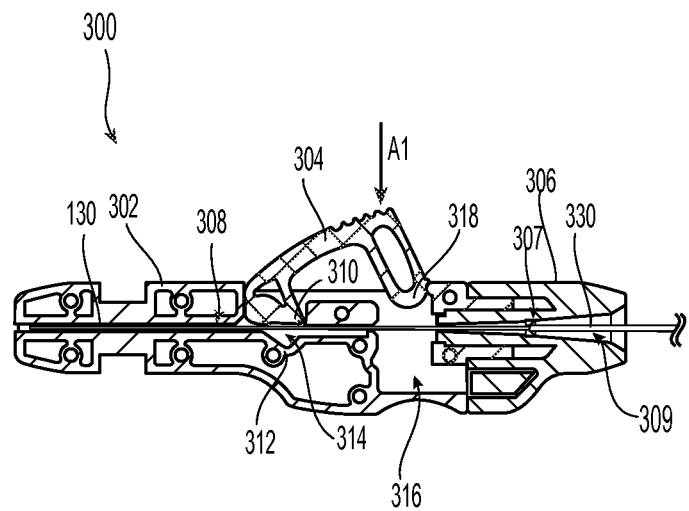
FIGS. 3C-3E are cross-sectional side views of the handle assembly of FIGS. 3A and 3B, shown moving from the retained state to a released state and coupled to an elongated member configured in accordance with the present technology.
Figure 3D:
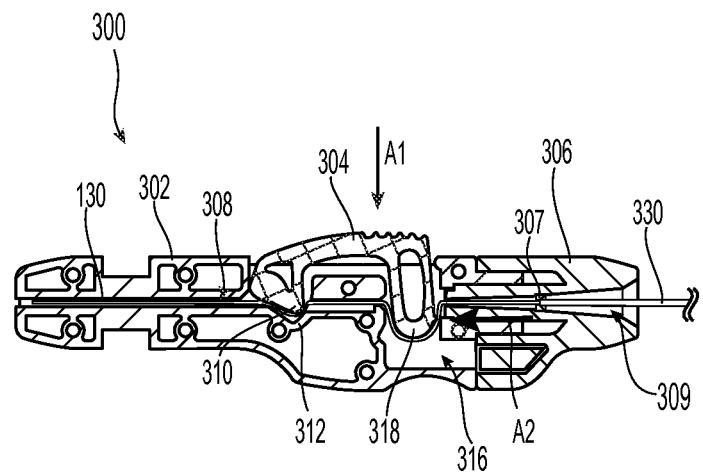
Figure 3E:
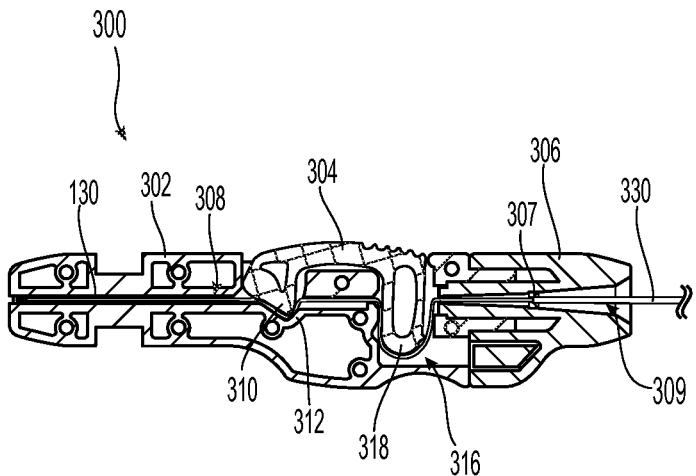

Referring to FIG. 3B, the housing 302 can include a channel 308 extending along at least a portion of its length and configured to slidably receive at least a portion of the elongated member 130 (as shown in FIGS. 3C-3E). The housing 302 can further include one or more recesses or cavities adjacent to the channel 308. For example, as shown in FIG. 3B, in some embodiments the housing 302 can include a first recess 314 and a second recess 316 located distally of the first recess 314 along the channel 308. The first and second recesses 314, 316 can be configured to receive the first and second protrusions 310, 318 of the lever 304 as the lever 304 moves into the released state.

The collar 306 can include a lumen 309 extending along at least a portion of its length and configured to slidably receive the elongated member 130 therethrough. In some embodiments, the lumen 309 can include a first portion 309a having a first diameter and a second portion 309b having a second diameter greater than the first diameter and located distal to the first portion 309a along the length of the lumen 309. The second portion 309b, for example, can be configured to receive an elongated outer member 330 (FIGS. 3C-3E) (e.g., an elongated shaft, a delivery sheath, etc.) configured to receive the elongated member 130 slidably therethrough. The outer member 330 can have an outer diameter that is greater than the first diameter of the first portion 309a; as such, the smaller diameter of the first portion 309a restricts the outer member 330 from moving proximally of the second portion 309b. In some embodiments at least a portion of the lumen 309 can be tapered in a distal direction. Additionally or alternatively, the lumen 309 can include a stepped portion 307 between the first portion 309a and the second portion 309b. In these and other embodiments, the lumen 309 can optionally include a tapered or stepped insert positioned within the lumen 309 (e.g., at the stepped portion 307).

In some embodiments, the collar 306 can be removably coupled to the housing 302 via one or more mechanical coupling mechanisms known in the art (e.g., a push tab 305 (shown in FIG. 3A), a spring-loaded pin, one or more threaded surfaces, etc.). In other embodiments, the collar 306 can be fixed to the housing 302 and/or be integral with the housing 302.

FIGS. 3C-3E are cross-sectional side views of the handle assembly 300 shown coupled to a portion of the elongated member 130 and outer member 330. As demonstrated by FIGS. 3C-3E, the handle assembly 300 can be moved between the retained state and the released state to decouple the implantable device (not shown) from the detachment system. In the retained state, as shown in FIG. 3C, the elongated member 130 can extend distally from a proximal portion of the channel 308, across first and second recesses 314, 316 and through at least a portion of the collar lumen 309 and the outer member 330. In the retained state, the elongated member 130 is free to slide axially through the channel 308 and lumen 309.

Such freedom of movement can be advantageous, for example, during insertion of the elongated member 130 through the tortuous vascular.

The handle assembly 300 can be moved to the released state by moving (e.g., pushing, rotating, bending, etc.) the lever 304 towards the channel 308 in the direction of arrow A1. FIG. 3D shows the handle assembly 300 in an intermediate state. As shown in FIG. 3D, as the lever 304 rotates or pivots towards the channel 308, the first and second protrusions 310, 318 also rotate or move towards the channel 308 and engage the elongated member 130. In the embodiment shown in FIGS. 3D-3E, the lever 304 is configured such that the first protrusion 310 crosses into the channel 308 before the second protrusion 318, and thus the first protrusion 310 engages the elongated member 130 before the second protrusion 318. As such, the first protrusion 310 pushes the elongated member 130 into the first recess 314 (FIG. 3C) and traps a portion of the elongated member 130 against a backstop 312 in the housing 302, thereby preventing axial movement of the elongated member 130 in a distal direction when the second protrusion 318 contacts and pushes against the elongated member 130. In other embodiments, the first and second protrusions 310 and 318 can engage the elongated member 130 at substantially the same time. In yet other embodiments, the lever 304 can include a single protrusion (e.g., the second protrusion 318).

As the second protrusion 318 pushes a portion of the elongated member 130 out of the channel 308 and into the second recess 316, the elongated member 130 bends out of alignment. Because a portion of the elongated member 130 proximal of the portion being engaged by the second protrusion 318 is held stationary (relative to the housing 302) by the first protrusion 310, the bending of the elongated member 130 by the second protrusion 318 forces the remaining portion of the elongated member 130 (distal of recess 316) to move proximally (as indicated by arrow A2), thereby releasing the implantable device 120 (FIG. 1A) from the detachment system.

In some instances, it may be desirable to detach the housing 302 and lever 304 from the collar 306. Because the elongated member 130 is fixed to the housing 302 and the lever 304 (in the released state, FIG. 3E), as the housing 302 and lever 304 are separated from the collar 306, the elongated member 130 can be pulled proximally through the outer member 330 and removed.

The handle assembly 300 of the present technology provides several advantages over conventional handle assemblies. For example, several conventional handle assemblies employ gripping mechanisms that grab the release mechanism (such as a release wire) in order to pull the release mechanism proximally and detach the implant. However, such "grab and pull" mechanisms can be prone to slippage because of the moisture inherently present in intravascular and/or surgical procedures (e.g., from blood, saline, or other fluids). Such moisture can cause the gripping mechanism to slide on the release wire, which prevents or delays pullback of the release wire. The handle assembly 300 of the present technology avoids these issues by pushing or bending the elongated member 130 to achieve proximal movement of the elongated member 130.

III. Additional Embodiments of Detachment Systems and Associated Devices and Methods FIGS. 4A and 4B are top and side views, respectively, of another embodiment of a detachment system 400 (also referred to as the "system 400") in a retained state configured in accordance with the present technology. Referring to FIGS. 4A-4B together, the system 400 can include a catheter 410, an implantable device 420, and an elongated member 430. The implantable device 420 and elongated member 430 of FIGS. 4A-4B can be generally similar to the implantable device 120 and elongated member 130 of FIGS. 1A-2D. For example, the implantable device 420 can include a hub 424, an expandable component 427 coupled to the hub 424, and a second coupling element 422 coupled to and extending distally from a proximal portion of the hub 424 and/or the expandable component 427. The implantable device 420 can include an elongated cavity 428 at a proximal portion of the device 420.

The catheter 410 can include an elongated shaft 414 configured to be intravascularly positioned at a treatment site within a blood vessel of a human, and a first coupling element 412 attached to and extending distally from the shaft 414. The elongated shaft 414 includes a proximal portion (not shown) and a distal portion 415. As shown in FIG. 4A, the first coupling element 412 is coupled to an outer surface 411 of the distal portion 415 of the shaft 414 (e.g., via adhesive, soldering, welding, and/or other suitable mechanical fixation means). In other embodiments, the first coupling element 412 can be coupled to an inner surface of the shaft 414. In some embodiments, the first coupling element 412 can be u-shaped with a first end portion (e.g., first leg) 412a fixed to one side of the shaft 414, a second end portion (e.g., second leg) 412b fixed to the other side of the shaft 414, and an intermediate portion 412c extending between the first and second end portions 412a-b. As such, the first coupling element 412 and the distal portion 415 of the shaft 414 can together define a closed loop surrounding an opening 416. In the illustrated embodiment, at least a portion of the intermediate portion 412c is curved. In other embodiments, the intermediate portion 412c can have other suitable shapes and configurations (e.g., a square shape, a triangular shape, etc.).

In some embodiments, the first coupling element 412 can be rigid, (e.g., a sufficiently thick stainless steel or polymer) and the second coupling element 422 can be flexible (e.g., a suture, a thin wire, etc.). In other embodiments (not shown), the first coupling element 412 can be flexible, and the second coupling element 422 can be rigid. In still other embodiments, the first and second coupling elements 412, 422 can be rigid or can both be flexible.

In the retained state, the elongated member 430 extends distally from the shaft 414 through the opening 426 in the second coupling element 422 (FIG. 4A) to the cavity 428 of the implantable device 420. The first coupling element 412 can extend distally from the shaft 414, and an inclined portion 423 of the second coupling element 422 can extend through the opening 416 (FIG. 4A) of the first coupling element 412. As such, the relative positioning of the elongated member 430, the first coupling element 412, and the second coupling element 422 secures the implantable device 420 to the shaft 414.

In some embodiments, in the retained state, the elongated member 430 can be positioned at a first elevation E1 and the first coupling element 412 can be positioned at a second elevation E2 that is different than the first elevation E1. The second coupling element 422 can extend distally from the hub 424 and/or implantable device 420 at a third elevation E3, pass through the first coupling element 412, and go around the elongated member 430 at a fourth elevation E4. Both the third elevation E3 and fourth elevation E4 can be different from the first elevation E1 and the second elevation E2. For example, in some embodiments, the fourth elevation E4 can be above the first elevation E1, the first elevation E1 can be above the second elevation E2, and the second elevation E2 can be above the third elevation E3. As shown in FIGS. 5A-5B, retraction of the elongated member 430 in a proximal direction (as indicated by arrow A), releases the implantable device 420 from the catheter 410.

Figure 6:
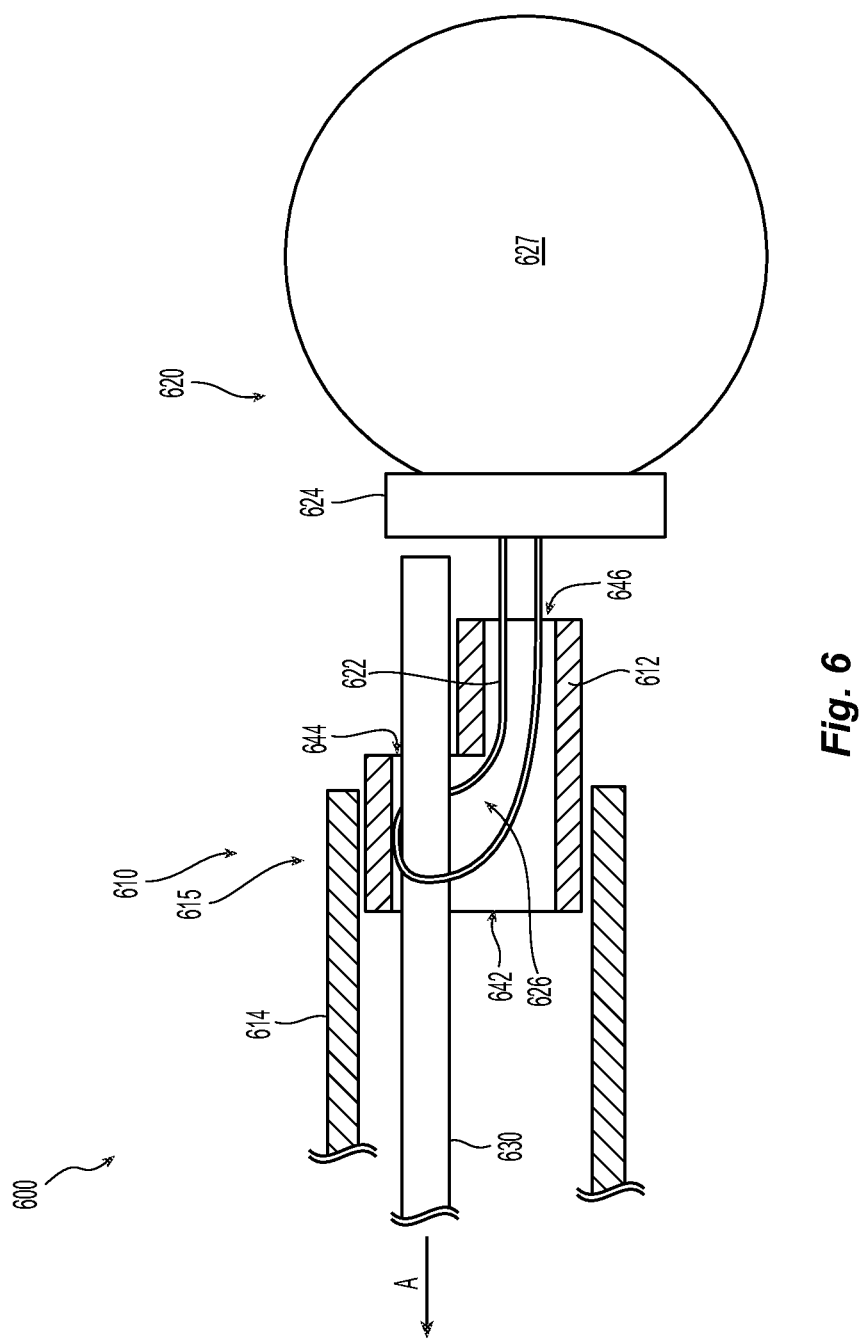
FIG. 6 is a partial cross-sectional side view of a detachment system in a retained state configured in accordance with another embodiment of the present technology.

FIG. 6 is a partial cross-sectional side view of another embodiment of a detachment system 600 configured in accordance with the present technology. The implantable device 620 and elongated member 630 shown in FIG. 6 can be generally similar to the implantable device 120 and elongated member 130 described with reference to FIGS. 1A-2D. As shown in FIG. 6, the system 600 can include a first coupling element 612 carried by, coupled to, and/or otherwise associated with a distal portion 615 of an elongated shaft 614. The first coupling element 612 can include a first opening 642, a second opening 644, and a third opening 646. As such, the first coupling element 612 includes two lumens: a first lumen extending between the first opening 642 and the second opening 644, and a second lumen extending between the first opening 642 and the third opening 646. When the system 600 is in the retained state, a second coupling element 622 can extend proximally from a hub 624 of the implantable device 620 through the third opening 646 and a portion of the second lumen, and the second coupling element 622 can be angled such that an opening 626 of the second coupling element 622 is at least partially aligned with the first lumen. In the retained state, the elongated member 630 can extend through the first opening 642, an opening 626 in the second coupling element 622, and the second opening 644 to interlock the first coupling element 612 and the second coupling element 622 and thereby prevent the implantable device 620 from detaching from the shaft 614. Proximal withdrawal of the elongated member 630 through the first and second coupling elements 612, 622 releases the implantable device 620 from the shaft 614.

Figure 7:
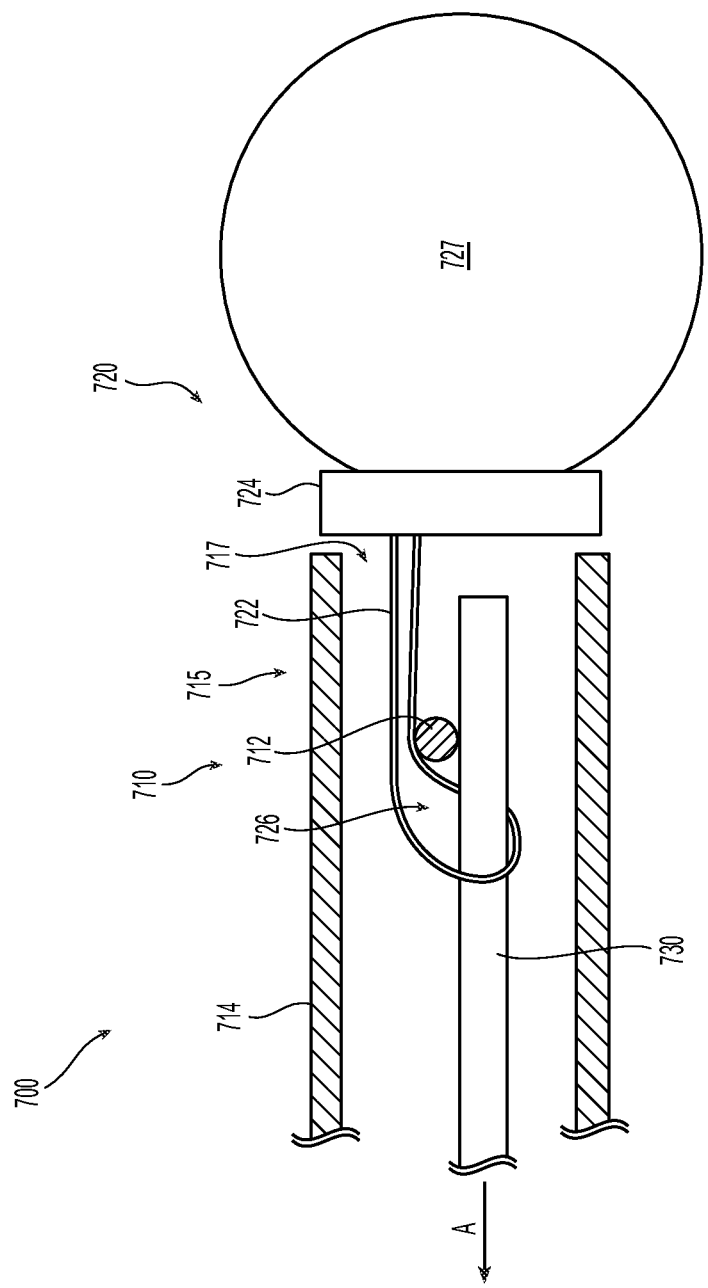
FIG. 7 is partial cross-sectional side view of a detachment system in a retained state configured in accordance with another embodiment of the present technology.

FIG. 7 is a partial cross-sectional side view of a detachment system 700 configured in accordance with another embodiment of the present technology. The implantable device 720 and elongated member 730 shown in FIG. 7 can be generally similar to the implantable device 120 and elongated member 130 described with reference to FIGS. 1A-2D. As shown in FIG. 7, the system 700 can include a first coupling element 712 carried by, coupled to, and/or otherwise associated with a distal portion 715 of an elongated shaft 714. In the embodiment shown in FIG. 7, the first coupling element 712 is a rod that extends across the diameter of the shaft 714 at the distal portion 715. When the system 700 is in the retained state, a second coupling element 722 extends proximally from a hub 724 of the implantable device 720 into a lumen 717 of the shaft 714 to a location proximal of the first coupling element 712, and the elongated member 730 extends distally through an opening 726 in the second coupling element 722 to a location aligned with or distal of the first coupling element 712. In this position, the elongated member interlocks the first coupling element 712 with the second coupling element 722 such that the implantable device 720 is retained with the shaft 714. Proximal withdrawal of the elongated member 730 through the second coupling element 722 to a position proximal of the first coupling element 712 releases the implantable device 720 from the shaft 714.

FIG. 8 is a partial cross-sectional side view of another embodiment of a detachment system 800 configured in accordance with the present technology. The system 800 shown in FIG. 8 can be generally similar to the system 700 described with reference to FIG. 7, except the shaft 814 in the embodiment shown in FIG. 8 includes an opening 802. In some embodiments, the opening 802 can be positioned proximal of the first coupling member 812. For example, during manufacturing, the opening 802 can be used to confirm that the second coupling element 822 is properly looped around and under the elongated member 830.

IV. Conclusion

Although many of the embodiments are described above with respect to devices, systems, and methods for retaining and releasing an implantable device within or near a cerebral aneurysm, other applications and other embodiments in addition to those described herein are within the scope of the technology. For example, the devices, systems, and methods of the present technology can be used to retain and detach an implantable device within or near any body cavity or lumen or walls thereof (e.g., arterial blood vessels, venous blood vessels, urological lumens, gastrointestinal lumens, the left atrial appendage, etc.). Additionally, several other embodiments of the technology can have different states, components, or procedures than those described herein. Moreover, it will be appreciated that specific elements, substructures, advantages, uses, and/or other features of the embodiments described with reference to FIGS. 1A-8 can be suitably interchanged, substituted or otherwise configured with one another in accordance with additional embodiments of the present technology. Furthermore, suitable elements of the embodiments described with reference to FIGS. 1A-8 can be used as standalone and/or self-contained devices. A person of ordinary skill in the art, therefore, will accordingly understand that the technology can have other embodiments with additional elements, or the technology can have other embodiments without several of the features shown and described above with reference to FIGS. 1A-8. For example, the detachment devices, systems, and methods of the present technology can be used with any of the implants and/or catheter devices, and systems disclosed in U.S. patent application Ser. No. 13/727,029, filed Dec. 26, 2012 and U.S. patent application Ser. No. 13/230,628, filed Sep. 11, 2011, both of which are incorporated by reference herein in their entireties.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A system for intravascular operation in a human, comprising:
   an elongated shaft configured to be intravascularly positioned at a treatment site within a blood vessel of a human, the elongated shaft defining a lumen therethrough, wherein the elongated shaft has a distal portion with a central longitudinal axis, a first coupling element at the distal portion, the first coupling element having a first opening, and a detent positioned along a portion of the lumen; and
   an implantable device including a second coupling element having a second opening, wherein the implantable device has a central longitudinal axis;
   an elongated member configured to extend through the shaft, the elongated member including a protrusion extending radially outwardly from the elongated member at a location along the elongated member such that the protrusion abuts the detent of the elongated shaft at a distal-most position of the elongated member in which the elongated member engages the second coupling element and is prevented from further axial movement with respect to the shaft;

wherein the system has a retained state in which (a) the central longitudinal axis of the implantable device and the central longitudinal axis at the distal portion of the elongated shaft are generally aligned, (b) a portion of the second coupling element is located proximal to the first opening, and (c) the elongated member is positioned through the first opening and the second opening such that the implantable device is retained with the shaft, and wherein the system has a released state when the elongated member is removed from the second opening, and in the released state the first coupling element is configured to move proximally apart from the second coupling element with an axial displacement less than an outer diameter of the first coupling element at a location along the length of the first coupling element proximate the first opening.

2. The system of claim 1 wherein the second coupling element is flexible.

3. The system of claim 1 wherein, at least when the system is in the retained state, the second coupling element includes an inclined portion.

4. The system of claim 3 wherein, at least when the system is in the retained state, a portion of the inclined portion extends through the first opening.

5. The system of claim 1 wherein neither the first coupling element nor the second coupling element includes a ball-shaped portion.

6. The system of claim 1 wherein a proximal portion of the implantable device includes an elongated cavity, and the elongated member extends through the second opening and into at least a portion of the cavity in the retained state.

7. The system of claim 1 wherein the implantable device includes an expandable vascular occlusion device configured to at least partially fill an aneurysm.

8. The system of claim 1 wherein the implantable device includes an expandable component configured to at least partially fill a cerebral aneurysm.

9. The system of claim 1 wherein, in the retained state, the elongated member is positioned under a portion of the second coupling element and over a portion of the first coupling element, or vice versa.

10. The system of claim 1 wherein at least one of the first coupling element and the second coupling element is flexible.

11. The system of claim 1 wherein:
a first portion of a surface of the elongated member is longitudinally aligned with the first coupling element;
a second portion of the surface of the elongated member is longitudinally aligned with the second coupling element; and
wherein the first portion faces a first direction and the second portion faces a second direction opposite the first direction.

12. The system of claim 1 wherein the first coupling element is integral with the elongated shaft.

13. The system of claim 1 wherein the second coupling element is a flexible, u-shaped wire.

14. The system of claim 1 wherein, in the retained state, a portion of the second coupling element is positioned between a portion of the elongated member and a portion of the first coupling element.

15. The system of claim 1 wherein the first coupling element extends distally from the elongated shaft.

16. The system of claim 1 wherein at least one of the first coupling element and the second coupling element is rigid.

17. The system of claim 1 wherein at least one of the first coupling element and the second coupling element is flexible, and the other is rigid.

18. The system of claim 1 wherein, in the retained state, the elongated member is positioned between a portion of the first coupling element and a portion of the second coupling element.

19. The system of claim 1 wherein a portion of the first coupling element that engages the elongated member is at a first elevation, a portion of the second coupling element that engages the elongated member is at a second elevation, and a portion of the elongated member between the portion of the first coupling element and the portion of the second coupling element is at a third elevation between the first and second elevation.

20. The system of claim 1 wherein the second coupling element has a third opening, and wherein, in the retained state, the first coupling element extends through one of the second opening and the third opening and the elongated member extends through the other of the second opening and the third opening.

21. The system of claim 1 wherein, when the system is in the released state and as the elongated shaft moves proximally, the system is configured such that the first coupling element slides proximally along the second coupling element within a circumference of the elongated shaft.

22. The system of claim 1 wherein the coupling element is u-shaped and includes first and second legs joined at their respective proximal termini by an intermediate portion, and wherein at least a portion of the first leg and at least a portion of the second leg are positioned along and fixed to a proximal portion of the implantable device such that the coupling element and the proximal portion of the implantable device define a closed path.

23. The system of claim 1 wherein the detent extends inwardly within the lumen of the shaft.

24. The system of claim 1 wherein, when the elongated member is at its distal-most position relative to the shaft, a distal terminus of the protrusion is at or proximal to a proximal terminus of the detent.

25. A system for intravascularly implanting a device in a body lumen, comprising:
an elongated shaft defining a lumen therethrough, the elongated shaft having a proximal portion, a distal portion with a cross-sectional dimension, a central longitudinal axis at the distal portion, a detent extending inwardly within the lumen at the distal portion, and a first coupling element;
an implantable device including an expandable component and a second coupling element extending proximally of the expandable component, wherein the implantable device is retained at the distal portion of the elongated shaft;
an elongated member configured to (a) extend along the shaft and through the first and second coupling elements in a retained state and (b) move proximally to be removed from the second coupling element in a released state; and
wherein the elongated member is configured to slide within the shaft to a distal-most position and includes a protrusion extending radially outwardly along a portion of the length of the elongated member, wherein the elongated member, wherein, when the elongated member is at the distal-most position, the protrusion abuts the detent of the elongated shaft and the elongated member engages the second coupling element, and wherein at least one of the first or second coupling elements is configured to slide over the other as the elongated shaft is moved proximally of the implantable device.

26. The system of claim 25 wherein at least one of the first coupling element and the second coupling element is flexible.

27. The system of claim 25 wherein, at least when the system is in the retained state, the second coupling element has an inclined portion.

28. The system of claim 2 wherein the expandable component is a braided vascular occlusion device configured to at least partially fill a body cavity.

29. The system of claim 25 wherein the expandable component is a vascular occlusion device configured to at least partially fill a cerebral aneurysm.

30. The system of claim 25 wherein the second coupling element is a flexible wire.

31. The system of claim 25 wherein the second coupling element is u-shaped and includes a first leg and a second leg, and wherein:

the first leg has a portion positioned along and fixed to an interior surface of the implantable device at a first location; and the second leg has a portion positioned along and fixed to the interior surface of the implantable device at a second location different than the first location.

32. The system of claim 25 wherein the second coupling element is u-shaped and includes first and second legs joined at their respective proximal termini by an intermediate portion, and wherein at least a portion of the first leg and at least a portion of the second leg are positioned along and fixed to a proximal portion of the implantable device such that the second coupling element and the proximal portion of the implantable device define a closed path.

33. The system of claim 25, wherein, at least when the elongated member is in the retained state, the second coupling element includes an inclined portion.

34. The system of claim 33 wherein, at least when the elongated member is in the retained state, a portion of the inclined portion extends through an opening in the first coupling element.

35. The system of claim 25 wherein neither the first coupling element nor the second coupling element includes a ball-shaped portion.

36. The system of claim 25 wherein a proximal portion of the implantable device includes an elongated cavity and, when the elongated member is in the retained state, the elongated member extends into at least a portion of the cavity in the retained state.

* * * * *